United States Patent [19]  
Muzzarelli

[11] 4,282,351  
[45] Aug. 4, 1981

[54] CHITOSAN-GLUCAN COMPLEX, METHOD FOR ITS PRODUCTION AND END USES

[75] Inventor: Riccardo Muzzarelli, Ancona-sap-Anico, Italy

[73] Assignee: Anic, S.p.A., Palermo, Italy

[21] Appl. No.: 45,002

[22] Filed: Jun. 4, 1979

[30] Foreign Application Priority Data

Jun. 14, 1978 [IT] Italy ................... 625 A/78

[51] Int. Cl.$^3$ .................... C08B 37/08; C07G 7/00
[52] U.S. Cl. ................... 536/20; 424/180
[58] Field of Search ................... 424/180; 536/20

[56] References Cited

U.S. PATENT DOCUMENTS

| | | | |
|---|---|---|---|
| 2,910,408 | 10/1959 | Pope et al. | 536/20 |
| 3,133,856 | 5/1964 | Neely | 536/20 |
| 3,892,731 | 7/1975 | Austin | 536/20 |

OTHER PUBLICATIONS

Beran, et al., "Chem. Abst.", vol. 78, 1973, p. 4,0141(p).
Bomstein, "Chem. Abst.", vol. 82, 1975, p. 15,534(u).
Shinoda, et al., "Chem. Abst.", vol. 84, 1976, p. 150,870(g).

*Primary Examiner*—Johnnie R. Brown
*Assistant Examiner*—Blondel Hazel
*Attorney, Agent, or Firm*—Morgan, Finnegan, Pine, Foley & Lee

[57] ABSTRACT

A method for preparing a chitosan-glucan complex is disclosed, which comprises the steps of subjecting filamentary fungal masses from certain fungal species such as Allomyces, Aspergillus, Penicillium, Mucor, Phycomyces, Choanephora, Zygorrhynchus and like fungi, to a treatment with a concentrated aqueous solution of a strong alkali brought to its boiling point and for a time of from 4 to 6 hours. This treatment removes a number of undesirable components since a deacetylation of chitin occurs, the soluble components being concurrently removed.

Foaming substances, if present, may be removed by a preliminary treatment with a solution of strong alkalies, with a lower concentration than that of the solution used for chitin deacetylation.

The products thus obtained lend themselves well to the preparation of columns capable of retaining certain compounds or elements, e.g. transition metal ions and can be used for flocculation reaction, in chromatographic reactions and many other uses.

6 Claims, 3 Drawing Figures

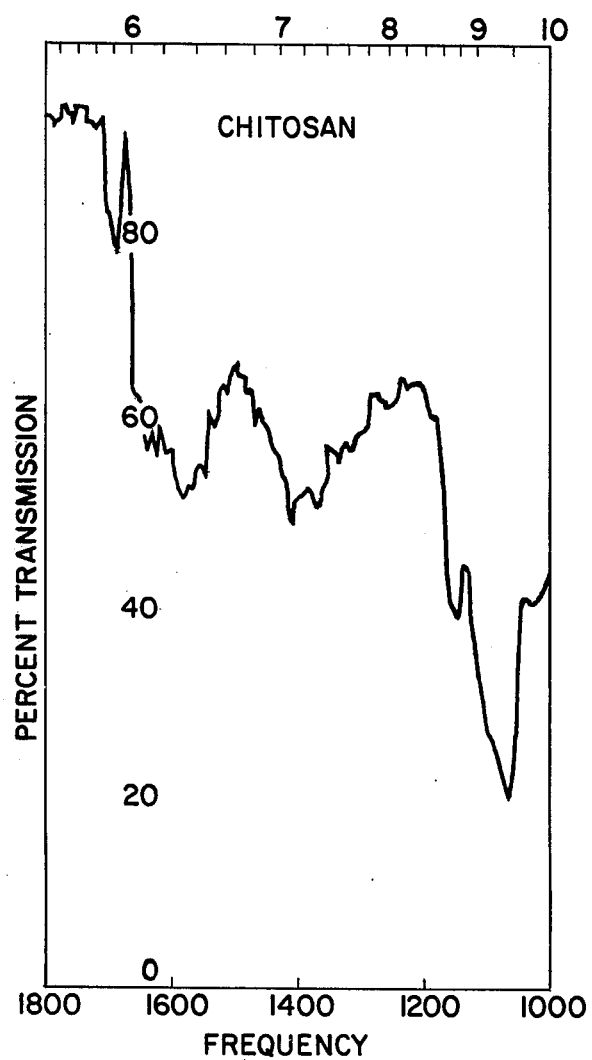
FIG. IC

CHITOSAN-GLUCAN COMPLEX, METHOD FOR ITS PRODUCTION AND END USES

FIELD OF THE INVENTION

The present invention relates generally to the production of a polysaccharide complex. It relates in particular to the production method and end uses of the chitosan-glucan complex having polyelectrolyte behavior, film forming capacity, chelating capacity and high hydrophilicity.

PRIOR ART

Polysaccharides of natural origin such as starch and cellulose have enormous importance in our technological world, because they are readily available and possess unique features unmatched by polymers of artificial production. Chitin, however, while as abundant as cellulose, is less easily made available mainly because it occurs in combinations with undesirable substances, from which so far it has had to be isolated and purified. The raw material in which chitin is combined with only one major component is a by-product of the fishing industry, i.e. the crustacean shells from which chitin can be isolated after dissolving calcium carbonate with acids.

Other sources, both of animal and fungal origin, have so far attracted much less attention, because their by-products are not so simple or storable as crustacean shells; for instance, krill and termites can be considered chitin sources, but, unless their proteins become useful for some kind of consumption, thus justifying the immediate processing of the catch, the extraction of chitin is absolutely uneconomical.

The by-products of fermentation processes, on the other hand, also contain chitin accompanied by other biopolymers, mainly glucans, mannans, proteins and lipids; they are normally incinerated as soon as they are separated from the culture media or the fermentation tanks because their storage is unhealthy and uneconomical.

Thus, in waste products other than crustacean shells, two unfavourable features have so far prevented their exploitation for chitin production: the heterogeneity of their composition and their rapid deterioration.

While chitin and chitosan have formed subject-matter of several patents, and though their applications are feasible, their costs are still high owing to the acidic-treatment required for the isolation of chitin from prevailing amounts of calcium carbonate (up to 90% dry weight).

The particular properties of chitosan are not found all together in any single man-made polymer. Chitosan, therefore, while still somewhat highly priced, becomes increasingly attractive for a series of applications.

SUMMARY OF THE INVENTION

Accordingly, it is the primary object of this invention to provide a highly efficient, exceedingly economical chitosan of constant quality, in combination with a polysaccharide whose presence not only does not limit or impede the most significant applications of chitosan, but enhances its qualities for the applications which form further objects of this invention.

This object is achieved, and the limitations of the prior art are obviated by simultaneously removing both the interfering components and the acetyl groups from the biomasses that originate from well-established industrial fermentation processes, especially from fungi, molds and yeasts. Such simultaneous removals are carried out with a single chemical, namely a strong alkali, at temperatures close to the boiling point of the solutions; in this way, previously useless wastes supply useful chitinous material instead of being incinerated, The product obtained is the chitosan-glucan complex where the glucan component surprisingly enhances the properties of chitosan.

Further objects of this invention are the applications of the chitosan-glucan complex, special emphasis being given to the collection of transition metal ions, to the flocculation of organic and inorganic matter, the precipitation of polyelectrolytes, the preparation of films and membranes and chromatographic aids for separations or for the immobilization of enzymes and catalysts.

DETAILED DESCRIPTION OF THE PREFERRED EMBODIMENTS

Figure 1A:
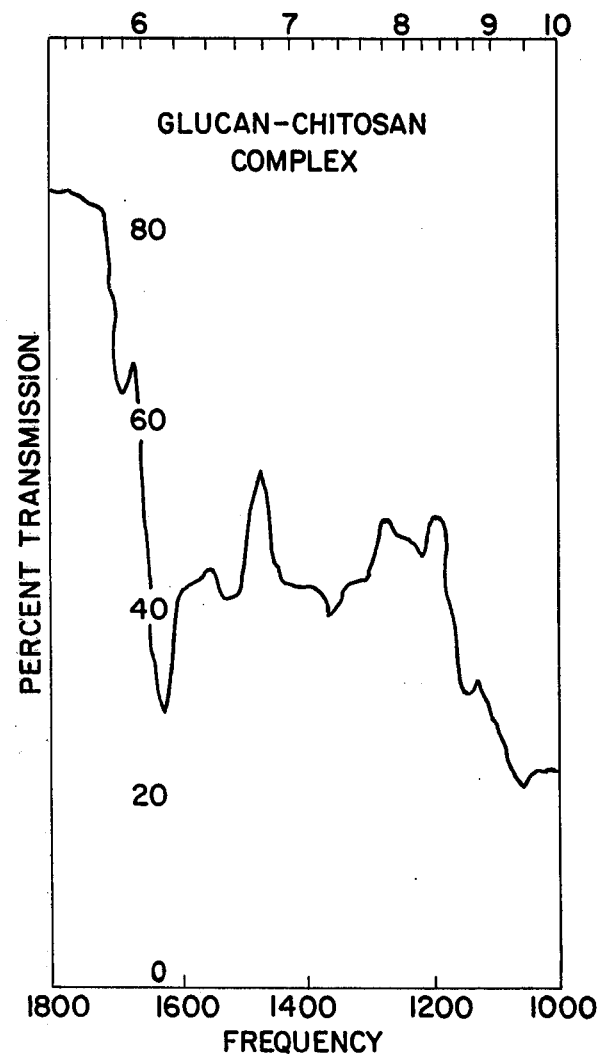

For a complete understanding of the present invention, reference should be made to the description of the preferred embodiments, which is set forth in detail hereinafter.

The treatment with sodium hydroxide of a biomass obtained from fungi, yeasts or molds has as its aim the simultaneous removal of soluble components and the conversion of chitin into chitosan by deacetylation, according to this invention. While the deacetylation requires concentrated sodium hydroxide, the removal of certain components requires merely dilute sodium hydroxide; therefore, to save on the alkali, a pre-treatment can, when necessary, be provided for to remove foaming substances.

In the typical process, the biomass is treated with 30–50% sodium hyroxide aqueous solution at the boiling temperature (118°–130° C.) for 4–6 hours. In these conditions, chitosan-glucan complexes are obtained having more or less pronounced characteristics.

Low temperature, short treatment times and low sodium hydroxide concentrations remove the soluble glucan less efficiently and lead to limited deacetylation, thus producing complexes of lower amine content with higher yields. This treatment of course removes all proteins and lipids.

The titration of chitosan in the chitosan-glucan complex is readily carried out with potassium polyvinylsulfonate (KPVS) (2.5 mM), indicator Toluidine Blue, on a dispersion of the complex (2 g) in 5% acetic acid (1:1). Under these conditions, 1 ml of KPVS is equivalent to 0.45 mg of chitosan. The completeness of the deacetylation can be also verified by X-ray diffraction spectrometry, by observing the absence of the diffraction peak at 26°21′, which is typical of chitin, and by measuring the ratio of the amine and amide bands in the infrared spectrum.

One of the peculiar features of the chitosan-glucan complex, surprisingly discovered according to this invention, is its collection capacity for manganous ions. The latter are very poorly collected by animal chitosan and separations of manganese from accompanying metal ions have been proposed in the prior art. On the contrary, the chitosan-glucan complex efficiently collects manganese, thus offering evidence of the differences between the chitosan-glucan complex and animal chitosan.

While it is known that certain fungi already contain some chitosan, since they possess the enzyme chitin deacetylase, it is likewise demonstrated that the said enzyme deacetylates only a limited part of the acetylamino groups present in newly synthesized chitin; in fact, chitosan in fungi is always accompanied by chitin.

The chitosan-glucan complex is therefore a novel composition of matter because, while being a complex chemical combination of two biopolymers only, it is, as a consequence of the treatment described in the present invention, also free from the undesirable acetyl groups, as shown by X-ray diffraction spectrometry and by other experimental evidence herein produced. No natural polymer matches the composition and the characteristics of the chitosan-glucan complex herein described, which are due to the chemical alterations made to the natural product.

The peculiar characteristics of the chitosan-glucan complex are in fact a consequence of the presence of the amino groups in the primary form and of the pre-existingchemical complexation of the two polymers. As proof of this, it should be noted that those desirable characteristics such as film forming capacity, chelating capacity, polyelectrolyte behavior are more pronounced when the deacetylation is carried out to the maximum extent. The chitosan-glucan complex is not simply a mixture of chitosan and glucan. Were this so, the chelating capacity of animal chitosan for metal ions would be higher than that of the same weight of chitosan-glucan complex, owing to the presence of glucan, which is known to have no chelating ability, as an isolated compound under the conditions adopted here.

On the contrary, it has been surprisingly discovered that the chitosan-glucan complex possesses higher chelating ability than the same weight of plain chitosan, as a result of particular steric arrangements of the amino and hydroxyl group in the complex, more propitious crystalline lattices and larger molecular size.

Figure 1B:
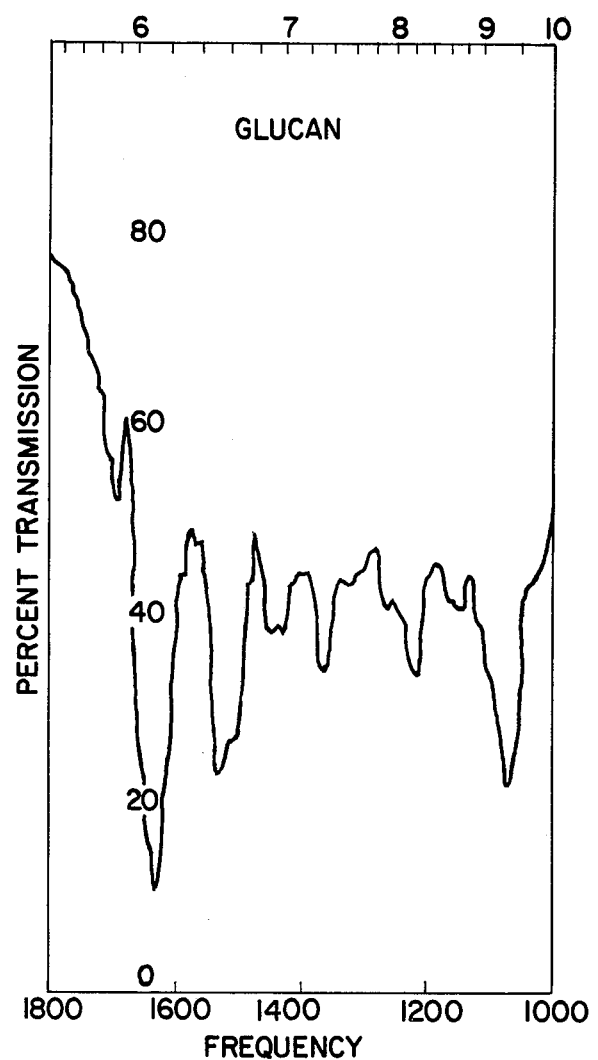

The infrared stectrum of the chitosan-glucan complex is shown in FIG. 1 A. The spectrum is chemically resolved by treating the complex in acetic acid and ultracentrifuging at 25,000 rpm. FIG. 1 B relates to the spectrum of solid glucan while the product obtained from the supernatant liquid on alkalinization has the spectrum shown in FIG. 1 C; the latter is identical to the chitosan spectrum, since the 1590 cm$^{-1}$ band of amino groups is present. The spectrum shown in FIG. 1 A also confirms that the chitosan-glucan complex is a novel composition of matter, which is reported for the first time in the present description of invention.

EXAMPLE 1

Production of the Chitosan-Glucan Complex

Yellow mycelial mats of *Mucor rouxii* from a culture medium comsisting of bread and water were treated with 40% sodium hydroxide solution for 4 hours at boiling (128° C.), to remove pigments, soluble polysaccharides, proteins and lipids, together with the acetyl groups of the chitinous components of the mycelia. The yield was 50% for a freeze-dried white powder containing 60% of chitosan. The same results were obtained when the Broussignac procedure was followed (potassium hydroxide in a mixture of glycol and ethanol).

EXAMPLE 2

Production of the chitosan-glucan complex

Black mycelial mats of *Aspergillus niger* from a citric acid production plant (1 Kg) were first washed with a 2.5% NaOH solution (10:1) for 30 min. The yield of the resulting fibrous powder was 50% since pigments, some soluble polysaccharides and part of the proteins and lipids were removed. The said product (500 g) was then treated with 40% sodium hydroxide solution (2.5:1) for 6 hours at boiling (128° C.), to remove the remaining parts of polymers and to perform the deacetylation, to obtain a white sample containing 32% of chitosan (yield 55% for a freeze-dried sample).

EXAMPLE 3

Collection of manganese

The chitosan-glucan complex powder (200 mg, 100–200 mesh), was stirred for 1 hour in 0.5 mM manganous sulfate solution (50 ml) at room temperature. The manganese collected on the chitosan-glucan complex was in the range of 40 to 82% of the amount available, depending on the choice of preparative conditions of the complex. Under the same conditions, the collection of manganese by animal chitosan was less than 10%.

EXAMPLE 4

Chromatographic separations of metal ions on the chitosan-glucan complex

Chromatographic columns of chitosan-glucan complex and of animal chitosan (200 mg) in water at pH 6 were used to treat solutions containing 10 ppm of zinc, copper, nickel and cobalt (sulfates) at a flow-rate of 2 ml/min. The effluent, in fractions of 10 ml, was analyzed by atomic absorption spectrometry. As shown in Table I, the chitosan-glucan complex is more effective than animal chitosan in removing metal ions from aqueous solutions. The data for zinc, nickel and copper are much higher for the complex than for animal chitosan, and even for copper, which did not yet saturate the columns after 800 ml. the capacity of the complex is better than that of animal chitosan.

| Ion | chitosan-glucan | animal chitosan |
|---|---|---|
| Zinc | 7 | 3 |
| Nickel | 21 | 10 |
| Cobalt | 10 | 3 |
| Copper | 67% (*) | 78% (*) |

(*) After 80 additions of 10-ml fraction each.

These data demonstrate that the nature of the complex, in spite of the lower nitrogen content, promotes the interaction of the metal ions with both the amino and hydroxyl groups, owing to the different physicochemical properties of the chitosan-glucan complex. The experimental data also indicate that the transition metal ions are separated from the alkali and alkali-earth elements, whose concentration is not altered after percolation through the columns. The chitosan-glucan complex can therefore abate the concentrations of transition metal ions in water to such an extent that they are no longer detected by the most sensitive analytical instrumentation available today.

EXAMPLE 5

Flocculation of dissolved and suspended matter in waters from olive oil production plants One liter of water from an olive oil production plant, whose solids content was 80 g/l and COD 130,000, was treated with 5 g of the chitosan-glucan complex, thus giving rise to the immediate flocculation of 70% of the dissolved and suspended matter, at pH 7, with a corresponding COD decrease to 30,000. The black product obtained was used as an animal feed supplement.

EXAMPLE 6

Precipitation of anionic polyelectrolytes

A solution of sodium alginate was prepared by dissolving 350 mg of alginic acid in water, adding sodium hydroxide to obtain a final solution of 0.1 M (100 ml). A dispersion of chitosan-glucan (175 mg) was prepared in water; 0.6 ml of glacial acetic acid was added to obtain 50 ml of a 0.2 M solution which was homogenized for 30 seconds. Upon mixing equal volumes of these two solutions, immediate precipitation occurred. The supernatant liquid was monitored by colorimetry to follow the sedimentation that rapidly occurred.

EXAMPLE 7

Preparation of chitosan-glucan membranes

A dispersion of the chitosan-glucan complex (1 g) in 5% acetic acid (20 ml), spread on a glass plate (20×20 cm) was dried at about 70° C. in an oven or over a water bath. The obtained film was washed with dilute sodium hydroxide and appeared flexible, transparent and yellow, and was quite pliable when hydrated, yet retained adequate strength to resist manipulations.

EXAMPLE 8

Preparation of thin layers for chromatography

A dispersion of the chitosan-glucan complex in a mixture of water and ethanol, preferably 80:20 by volume, was poured into a Desaga apparatus for thin layer-preparation. The layers so prepared were uniform, of constant thickness and suitable for chromatographic purposes.

EXAMPLE 9

Immobilization of enzymes on chitosan-glucan complex

A solution containing egg white lysozyme was used to permeate a column of the chitosan-glucan complex (8×160 mm); the lysozyme was completely retained in the column, where it maintained 70% of its original enzymatic activity, as shown by data obtained with the Glycolchitosan-Remazol Brilliant Blue method.

I claim:

1. A method of producing the chitosan-glucan complex having the infrared spectrum shown in FIG. 1 A comprising treating a biomass selected from yeast, mold and fungus containing chitin and glucan with a solution of a strong alkali having a concentration of 30 to 50% at a temperature up to the boiling point of said solution.

2. The method of claim 1 further comprising pretreating said biomass with a solution of a strong alkali having a concentration of less than 30% at a temperature lower than said treatment step.

3. The method of claims 1 or 2 wherein said alkali is sodium hydroxide and said biomass is a fungus selected from Allomyces, Aspergillus, Pencillium, Mucor, Phycomyces, Choanephora, Zygorrhynchus.

4. The method of claim 3 further comprising treating said biomass with a 30 to 50% sodium hydroxide aqueous solution at a temperature between 118° C. and 130° C. for four to six hours.

5. A method of chelating transition metals comprising contacting a solution containing said metals with a chitosan-glucan complex having the infrared spectrum shown in FIG. 1 A.

6. The method of claim 5 wherein said metals are selected from the group consisting of zinc, copper, nickel, cobalt, and manganese.

* * * * *